(12) United States Patent
Schlaps

(10) Patent No.: US 6,709,478 B2
(45) Date of Patent: Mar. 23, 2004

(54) ENGINE CRANK CASE SAMPLING SYSTEM

(75) Inventor: Erwin J Schlaps, St. Clair, MI (US)

(73) Assignee: DaimlerChrysler Corporation, Auburn Hills, MI (US)

(*) Notice: Subject to any disclaimer, the term of this patent is extended or adjusted under 35 U.S.C. 154(b) by 11 days.

(21) Appl. No.: 10/163,754

(22) Filed: Jun. 6, 2002

(65) Prior Publication Data
US 2002/0185009 A1 Dec. 12, 2002

Related U.S. Application Data
(60) Provisional application No. 60/296,313, filed on Jun. 6, 2001.

(51) Int. Cl.[7] .............................................. B01D 50/00
(52) U.S. Cl. ............................ 55/417; 55/467; 55/482; 55/482.1; 55/DIG. 19; 96/189; 96/413; 96/417
(58) Field of Search ............................... 55/315, 315.1, 55/315.2, 417, 467, 482, 482.1, DIG. 19; 96/188, 189, 413, 417

(56) References Cited

U.S. PATENT DOCUMENTS

| 423,653 | A | | 3/1890 | Abrams | |
|---|---|---|---|---|---|
| 3,754,538 | A | * | 8/1973 | Ephraim et al. | 123/41.86 |
| 3,868,222 | A | | 2/1975 | Barringer | |
| 3,939,694 | A | | 2/1976 | Guichard | |
| 3,965,748 | A | | 6/1976 | Boubel | |
| 4,861,359 | A | * | 8/1989 | Tettman | 55/419 |
| 5,196,170 | A | | 3/1993 | Patashnick | |
| 5,279,146 | A | | 1/1994 | Asano | |
| 5,279,970 | A | | 1/1994 | Patashnick | |
| 6,058,917 | A | | 5/2000 | Knowles | |

* cited by examiner

Primary Examiner—Robert A. Hopkins
(74) Attorney, Agent, or Firm—Edwin W. Bacon, Jr.

(57) ABSTRACT

A gas separator system for providing contaminant-free engine crankcase gas to a gas analyzer. The system has an inlet member for receiving the crankcase gas from the engine and an oil separator for separating at least a portion of the contaminants from the crankcase gas. A pump is arranged to draw the crankcase gas through the inlet member and move the separated crankcase gas to the gas analyzer.

21 Claims, 3 Drawing Sheets

ENGINE CRANK CASE SAMPLING SYSTEM

CROSS-REFERENCES TO RELATED APPLICATIONS

This application claims the benefit of U.S. Provisional Patent Application Ser. No. 60/296,313, filed Jun. 6, 2001.

FIELD OF THE INVENTION

This invention relates generally to an apparatus for measuring the level of gaseous pollutants in the crankcase of an internal combustion engine. More particularly, the apparatus continuously separates particulates and lubricating oil from crankcase gas to facilitate measuring gaseous pollutants of interest.

DESCRIPTION OF THE RELATED ART

Designers of internal combustion engines strive to reduce levels of pollutants generated in the engine. One carrier of pollutants is blow-by gas in the crankcase. This gas is typically recirculated by a Positive Crankcase Ventilation (PCV) system into the intake manifold of the engine where the gas flows into the combustion chamber to be burned. In order to optimize the design of the PCV system, it is desirable to measure, in real time, the level of pollutants in the blow-by gas. Once the level of pollutants is known it is possible to make changes to the engine control system, engine components and the PCV system to reduce pollutant levels.

One method of indirectly measuring pollutant levels is to perform a spectral analysis of oil used in the engine. With this method, the engine is operated under a prescribed operating condition for a specified period. At the end of the period, a sample of the engine oil is subjected to a spectral analysis that exposes the level of contaminants in the oil. The pollutant level in the blow-by gas is then inferred from the results of the spectral analysis and knowledge of the prescribed operating condition to which the engine was subjected. While the spectral analysis test is used by engine designers, it has two shortcomings. The first shortcoming is the time needed to produce measurements of pollutant levels. A typical specified period can be 10,000 miles of operation in an automobile. With such a long test period, engine designers are limited to running a few tests before an engine design must be ready for production. Second, the spectral analysis test only provides indirect information on the aggregate level of pollutant levels in the blow-by gas. The test does not provide pollutant levels as a function of time. This leaves the engine designer guessing what mode of engine operation produces the worst pollutant level.

BRIEF SUMMARY OF THE INVENTION

Accordingly, one aspect of this invention is to provide a system for facilitating measurement of pollutant levels in the crankcase gas of a running engine.

In accordance with this aspect, the present invention provides a gas separator system for providing contaminant-free engine crankcase gas to a gas analyzer. The system has an inlet member for receiving the crankcase gas from the engine and an oil separator for separating at least a portion of the contaminants from the crankcase gas. A pump is arranged to draw the crankcase gas through the inlet member and move the separated crankcase gas to the gas analyzer.

Further areas of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description.

DETAILED DESCRIPTION OF THE INVENTION

Figure 1:
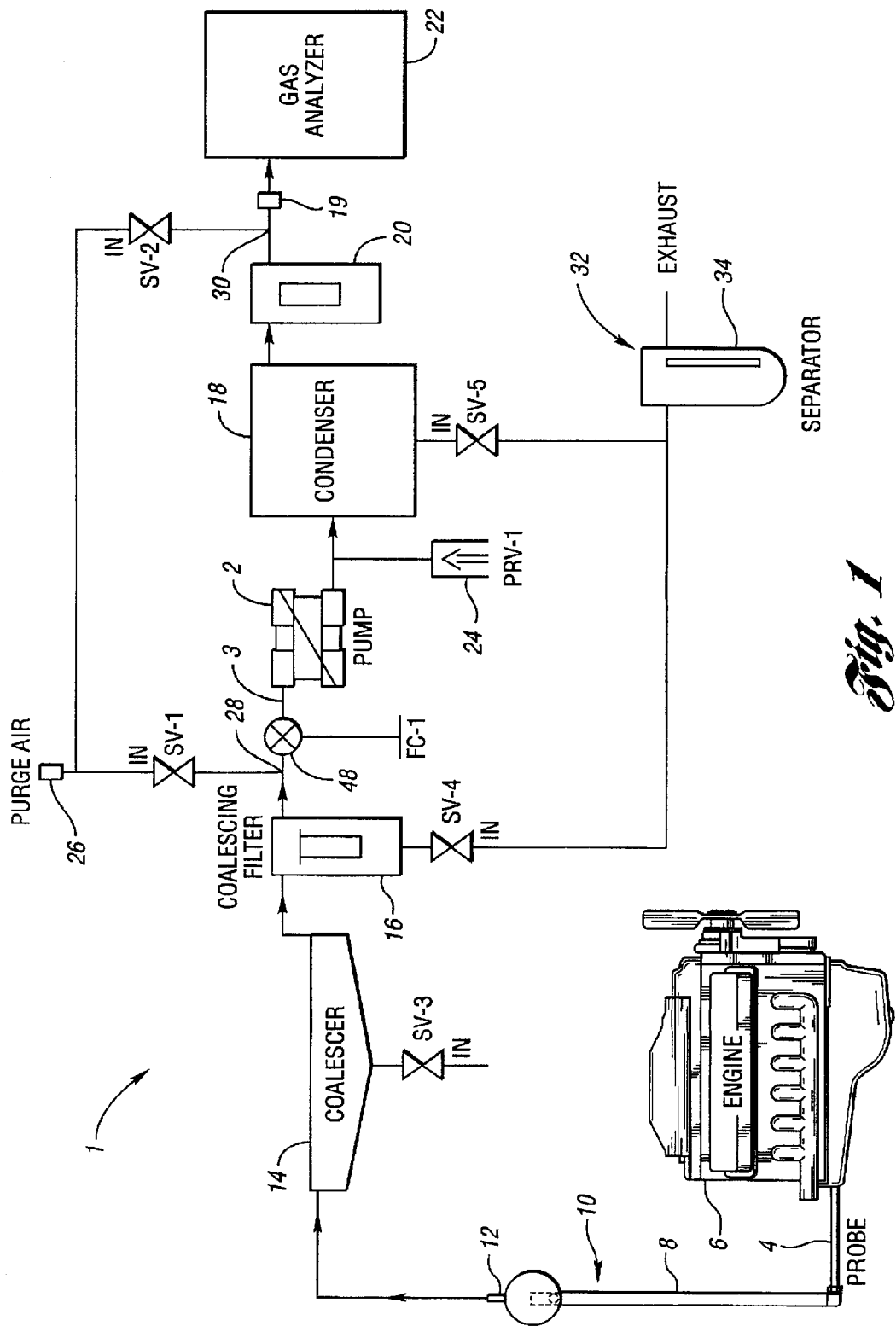
FIG. 1 is a pneumatic diagram of the apparatus.

FIG. 1 shows a pneumatic diagram of an engine crankcase gas sampling system 1. The system is generally constructed as a test fixture for use in an engine dynamometer cell, but may also be constructed as a piece of portable test equipment or incorporated into a vehicle. A vacuum pump 2 provides vacuum at intake 3 for drawing a continuous stream of blow-by gas through a probe 4 in the crankcase of the engine 6. The direction of the continuous stream is indicated by arrows drawn on the lines interconnecting components of the system 1. In an exemplar embodiment, the pump 2 is a four-head diaphragm type to provide a sufficient vacuum level with a minimum magnitude of pressure pulsations in the system 1. At the point the probe 4 is connected to the engine 6, the blow-by gas is contaminated with particulate matter, light ($<C_4$) and heavy ($>=C_5$) hydrocarbons, and engine oil in liquid and vapor phases. The contaminated blow-by gas is drawn by the vacuum through the probe 4 and into the standpipe 8 and oil separator 10. The standpipe 8 and oil separator 10 together separate a substantial portion of the liquid and vaporous oil from the blow-by gas. The gas velocity in the standpipe 8 is low enough to allow the separated oil to drip down the inside wall of the standpipe 8 and reenter the engine 6 via the probe 4.

At the output of the oil separator 10, the blow-by gas and oil vapor flow out through a nipple 12 and on to an optional coalescer 14. While not required, the coalescer 14 operates to separate additional liquid oil from the stream flowing out of the oil separator 10. Depending on the level of liquid oil entering the system through the probe 4, using the coalescer 14 to further lower the level of liquid oil may assist in extending the service interval of a downstream coalescing filter 16. If the coalescer 14 is not used, a simple fluid conduit may be interconnected between the nipple 12 and the input of the coalescing filter 16.

The coalescing filter 16 removes any remaining liquid and most, if not all, of the particulates from the contaminated blow-by gas. Any remaining oil vapor can be removed at a later stage by a condenser 18 (if used) and a hydrocarbon (HC) trap filter 20. Upon leaving the coalescing filter 16, the sampled blow-by gas is clean of particulate matter, liquid oil and a substantial amount of vaporous oil. The clean blow-by gas is then vacuumed into the pump 2 and expelled therefrom at an outlet pressure into the optional condenser 18. The flow rate and pressure of gas at the outlet of the pump 2 should be matched to the input requirement of a chosen gas analyzer 22. This match may be performed with regulator arrangement 19 at the inlet to the gas analyzer 22. Also at the outlet of the pump 2 is a pressure relief valve 24. The pressure relief valve 24 prevents excessive pressure from accumulating between the output of the pump 2 and the input to the gas analyzer 22 in the event the condenser 18, HC trap filter 20 or related plumbing become plugged. The relief pressure of the pressure relief valve 24 should be set greater than the outlet pressure of the pump 2. In an exemplar embodiment, a relief pressure of 25 PSIG is used with an outlet pressure of 15 PSIG.

The condenser 18 is desirable if, after passing through the coalescing filter 16 and pump 2, the clean blow-by gas still contains a level of vaporous oil that may prematurely clog or destroy the HC filter 20. If the condenser 18 is used, a condenser temperature in the range of approximately thirty-two to forty degrees Fahrenheit should be sufficient to remove remaining traces of oil vapor from the blow-by gas. In an embodiment where the condenser 18 is omitted, it may be replaced with a simple fluid conduit interconnecting the output of the pump 2 to the input of the HC trap filter 20.

The blow-by gas enters HC trap filter 20 prior to being pumped into the gas analyzer 22. The HC trap filter 20 removes the heavy hydrocarbons from the blow-by gas. Upon exiting the apparatus at the outlet of the HC trap filter 20, the blow-by gas has been filtered of contaminants and is in a condition for the gas analyzer 22 to accept and measure. Typical types of gas analyzers 22 used to analyze the blow-by gas include $CO_2$ and $NO_x$ analyzers.

Continuing to refer to FIG. 1, components are shown to facilitate purging the separated contaminants from the system 1 after a test is performed. To purge the system 1, an external compressed air source is attached at the purge air connector 26. In an exemplar embodiment, the compressed air source is regulated to about 40 PSIG. Purging commences by opening of solenoids SV-1, SV-2, SV-3 (if the coalescing sump is used), SV-4, and SV-5 (if the condenser is used.) With the solenoids opened, the regulated shop air flows through SV-1 into a first tee 28 and through SV-2 into a second tee 30. Purge air from the first tee 28 flows in a reverse direction through the coalescing filter 16 and, if used, the coalescing sump 14. Oil and residual blow-by gas are pushed by the purge air out of the coalescing filter 16 and through solenoid SV-4 to an exhaust system 32. A portion of purge air from the first tee 28 continues to flow in a reverse direction to the coalescing sump 14, where the sump 14 is purged through open solenoid valve SV-3. Purge air also flows through the oil separator 10 and standpipe 8, thereby returning oil trapped in those components to the engine 6.

Purge air from the second tee 30 flows in a reverse direction through the HC trap filter 20 and the condenser 18, if it is used. Purge air coming through the condenser 18 passes through the open solenoid valve SV-5 and into the exhaust system 32. Some purge air also moves forward toward the attached gas analyzer 22.

The exhaust system 32 collects the purge air from solenoid valves SV-4 and SV-5 (which is included only when the condenser is used) and passes the collected air through a separator 34. The separator 34 collects contaminants into a bowl that must be periodically emptied. Clean air is exhausted into the atmosphere after being processed by the separator 34.

An important consideration in using the apparatus is the rate at which the pump 2 draws vacuum to pull crankcase gas through the probe 4. It is undesirable to have the apparatus draw gas at a rate high enough to have a material effect on the PCV flow rate in the engine 6. A suggested guideline is to limit the system 1 to drawing gas at a rate less than 10% of the rate blow-by gas is produced by the engine 6. To achieve this limited flow rate, a flow control valve 48 may be inserted in the inlet stream of the pump 2. In an exemplar embodiment, the flow control valve 48 is set to a flow rate of eight standard cubic feet per hour (SCFH).

Figure 2A:
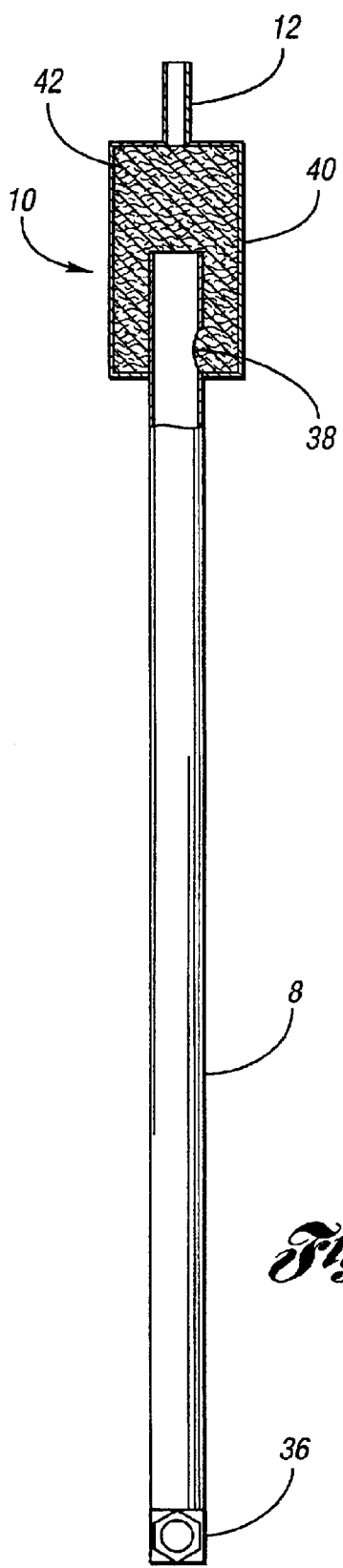
FIG. 2A is side view of the oil separator and standpipe assembly with a cross section of the oil separator housing.

Turning now to FIG. 2A, the standpipe 8 is shown together with a cross-section of the oil separator 10. The cross section is taken along section line 2A—2A of FIG. 2B. The standpipe 8 has the oil separator 10 at an outlet end and may have a probe connector 36 attached at a probe end. Stainless steel has been found a suitable material for the standpipe 8.

Figure 2B:
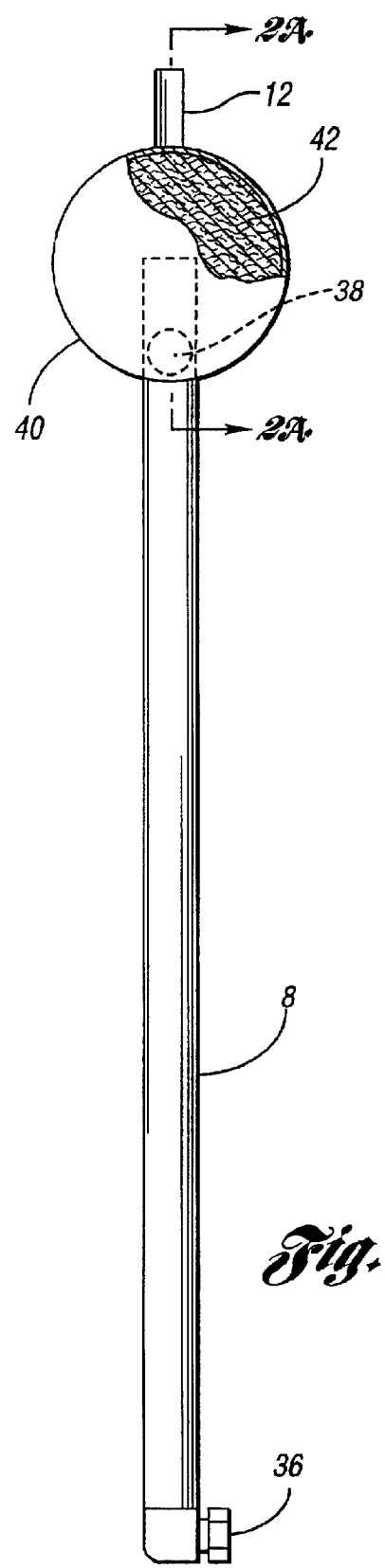
FIG. 2B is a front view of the oil separator and standpipe assembly.

As shown in FIG. 2B, the outlet end of the standpipe 8 is closed, and a hole 38 is formed in the wall of the standpipe 8 at a location such that the hole 38 is contained within the oil separator housing 40. The hole 38 should be formed as close to the edge of the oil separator housing 40 as possible so that oil flows from the separator 10 into the hole 38 and then down the standpipe 8 to the engine 6. The oil separator housing 40 is loosely filled with a fibrous material 42 such as woven copper mesh.

In operation, the standpipe 8 and oil separator 10 assembly is placed in a generally vertical position with probe connector 36 at the bottom. Gas drawn from the crankcase probe 4 enters the standpipe 8 and travels upward towards the oil separator 10. Oil in the crankcase gas accumulates on the interior wall of the standpipe 8 and drips back down to the engine 6. At the top of the standpipe 8, the gas may still contain engine oil vapor and some oil in liquid phase. The gas enters the hollow interior of the separator housing 40 via the hole 38 in the wall of the standpipe. The gas then flows through the fibrous material 42 and out through the nipple 12. Oil vapor condenses onto the fibrous material 42 while the gas flows through it. The condensed oil wicks out of the fibrous material 42 and is drawn by gravity to the lowest portion of the separator housing 40 where it drips though the hole 38 and back into the engine 6.

A trade-off should be considered when choosing the dimensions of the standpipe 8 and separator housing 40. A longer standpipe 8 and more voluminous separator housing 40 will be more effective at removing liquid and vaporous oil than shorter and smaller ones, respectively. However, the larger parts will undesirably increase the propagation delay of crankcase gas through them.

Figure 3:
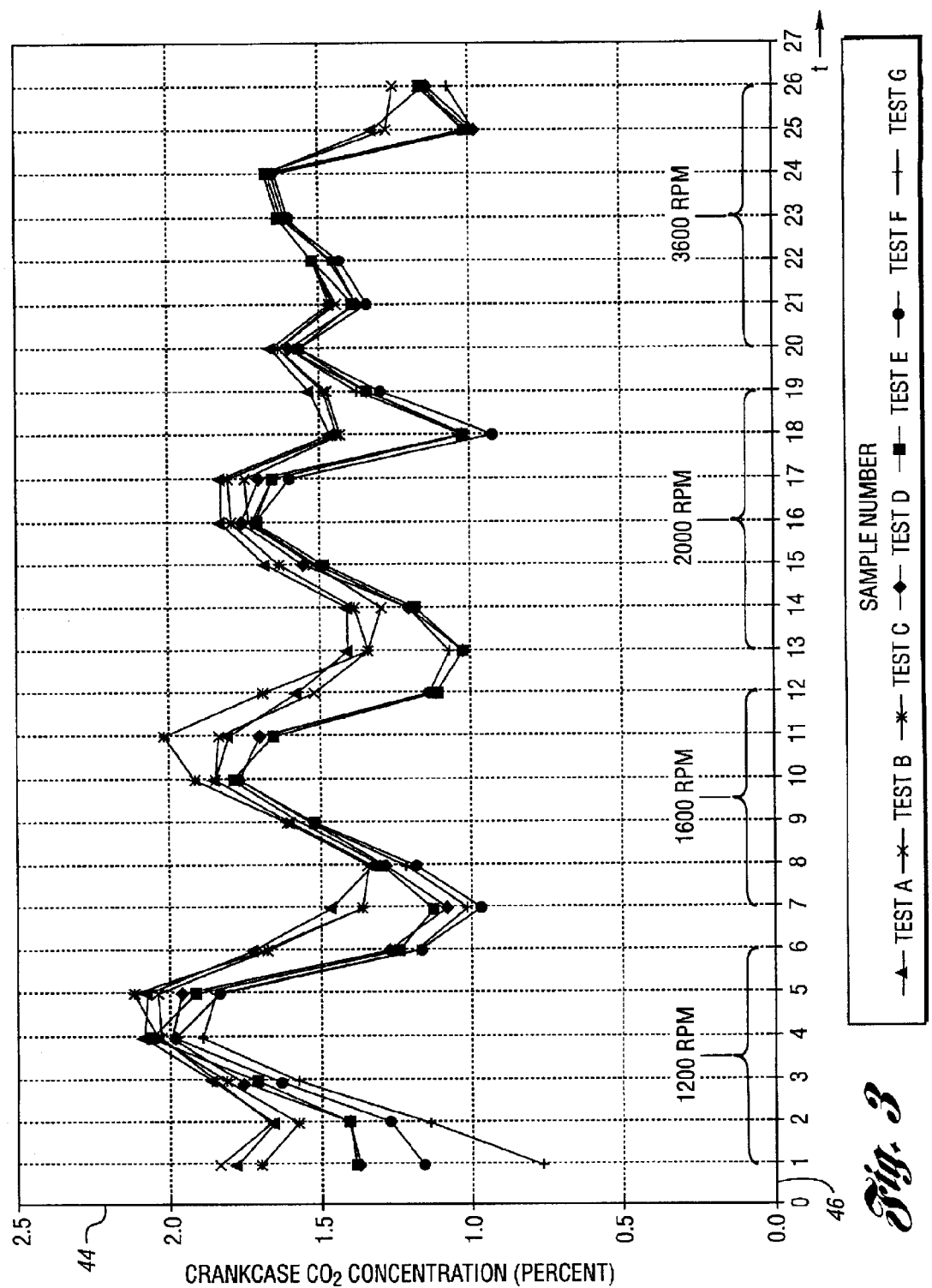
FIG. 3 is an example of crankcase gas data.

Turning now to FIG. 3, a graph is shown with an example of $CO_2$ pollutant data taken from blow-by gas. The blow-by gas was analyzed using a $CO_2$ gas analyzer 22. The vertical axis 44 of the graph represents crankcase $CO_2$ concentration in percent and the horizontal axis 46 represents time in minutes. In this graph, the engine 6 was running at 1200 RPM from the first through the sixth minute, at 1600 RPM from the seventh through the twelfth minute, 2000 RPM from the thirteenth minute to the nineteenth minute and at 3600 RPM from the twentieth through the twenty-sixth minute of the test. Load on the engine 6 was varied at each minute interval and the gas flow rate was allowed to stabilize through the system 1. At the end of each minute, the gas analyzer 22 produced a data point. The test was repeated several times as is indicated by the legend of FIG. 3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A gas separator and analysis system for testing engine crankcase gas, said system comprising:
an inlet member for receiving the crankcase gas;
an oil separator for separating at least a portion of the contaminants from the crankcase gas, said oil separator fluidly coupled to said inlet member, and
a pump arranged to draw the crankcase gas through said inlet member and move the separated crankcase gas to a gas analyzer via an outlet of said oil separator.

2. A gas separator system for providing contaminant-free engine crankcase gas to a gas analyzer, said system comprising:
an inlet member for receiving the crankcase gas;
an oil separator for separating at least a portion of the contaminants from the crankcase gas, said oil separator fluidly coupled to said inlet member;
a pressure relief valve arranged to prevent a pressure of separated crankcase gas from exceeding a maximum inlet pressure of the gas analyzer; and
a pump arranged to draw the crankcase gas through said inlet member and move the separated crankcase gas to the a gas analyzer via an outlet of said oil separator.

3. The system of claim 2 further comprising a standpipe, said standpipe being fluidly coupled between said inlet member and said oil separator.

4. The system of claim 2 wherein said oil separator contains a fibrous material for removing at least a portion of the contaminants from the crankcase gas.

5. The system of claim 4 wherein said fibrous material is woven copper mesh.

6. The system of claim 2 further comprising a coalescing filter fluidly coupled between said oil separator and the gas analyzer.

7. The system of claim 2 further comprising a flow control valve for regulating a flow rate of crankcase gas through the system.

8. The system of claim 7 wherein said flow control valve is arranged to maintain a flow rate less than ten percent of the flow rate that the engine generates crankcase gas.

9. The system of claim 2 further comprising a hydrocarbon filter fluidly coupled between said oil separator and the gas analyzer, said hydrocarbon filter operating to remove the remainder of the contaminants from the crankcase gas such that the separated crankcase gas is compatible with the gas analyzer.

10. A gas separator system for providing contaminant-free engine crankcase gas to a gas analyzer, said system comprising:
an inlet member for receiving the crankcase gas;
an oil separator for separating at least a portion of the contaminants from the crankcase gas, said oil separator fluidly coupled to said inlet member;
a condenser fluidly coupled between said oil separator and the gas analyzer; and
a pump arranged to draw the crankcase gas through said inlet member and move the separated crankcase gas to the gas analyzer via an outlet of said condenser.

11. The system of claim 10 wherein said condenser is arranged to operate at less than forty degrees Fahrenheit.

12. A gas separator system for drawing crankcase gas from an engine, separating contaminants from the crankcase gas, and providing the separated crankcase gas to a gas analyzer, said system comprising:
an inlet member for receiving the crankcase gas;
an oil separator fluidly coupled to said inlet member, said oil separator separating at least a portion of the contaminants from the crankcase gas;
a coalescing filter having an inlet and an outlet, said coalescing filter inlet being fluidly coupled to said oil separator;
a hydrocarbon filter having an inlet and an outlet, said hydrocarbon filter inlet being fluidly coupled to said coalescing filter outlet and said hydrocarbon filter outlet being adapted for providing separated crankcase gas to the gas analyzer; and
a pump arranged for maintaining flow of the crankcase gas into said inlet member.

13. The system of claim 12 further comprising a standpipe, said standpipe being fluidly coupled between said oil separator inlet and said inlet member.

14. The system of claim 12 wherein said oil separator contains a fibrous material for removing at least a fraction of the contaminants from the crankcase gas.

15. The system of claim 14 wherein said fibrous material is woven copper mesh.

16. The system of claim 12 further comprising a coalescer fluidly coupled between the said oil separator output and said coalescing filter input.

17. The system of claim 12 further comprising a condenser fluidly coupled between said coalescing filter and said hydrocarbon filter.

18. The system of claim 17 wherein said condenser is arranged to operate at less than forty degrees Fahrenheit.

19. The system of claim 12 further comprising a flow control valve for regulating a flow rate of crankcase gas through the system.

20. The system of claim 19 wherein said flow control valve is arranged to maintain a flow rate is less than ten percent of the flow rate that the engine generates crankcase gas.

21. The system of claim 12 further comprising a pressure relief valve arranged to prevent a pressure of separated crankcase gas from exceeding a maximum inlet pressure of the gas analyzer.

* * * * *